(12) United States Patent
Muggleton et al.

(10) Patent No.: US 8,126,823 B2
(45) Date of Patent: Feb. 28, 2012

(54) SUPPORT VECTOR INDUCTIVE LOGIC PROGRAMMING

(75) Inventors: Stephen Howard Muggleton, London (GB); Huma Mahmood Lodhi, Sunbury-on-Thames (GB); Michael Joseph Ezra Sternberg, Middlesex (GB); Ataollah Amini, London (GB)

(73) Assignee: Imperial Innovations Limited (GB)

( * ) Notice: Subject to any disclaimer, the term of this patent is extended or adjusted under 35 U.S.C. 154(b) by 818 days.

(21) Appl. No.: 12/066,689

(22) PCT Filed: Sep. 8, 2006

(86) PCT No.: PCT/GB2006/003320
§ 371 (c)(1),
(2), (4) Date: Aug. 8, 2008

(87) PCT Pub. No.: WO2007/031716
PCT Pub. Date: Mar. 22, 2007

(65) Prior Publication Data
US 2008/0301071 A1    Dec. 4, 2008

(30) Foreign Application Priority Data
Sep. 13, 2005    (GB) .................................. 0518665.5

(51) Int. Cl.
*G06F 15/18*    (2006.01)
(52) U.S. Cl. .......................................................... 706/12
(58) Field of Classification Search .................... None
See application file for complete search history.

(56) References Cited

U.S. PATENT DOCUMENTS
2003/0172043 A1    9/2003    Guyon et al.

FOREIGN PATENT DOCUMENTS
EP    1628234 A1    2/2006
WO    0247007 A2    6/2002

OTHER PUBLICATIONS

Gaertner et al., Kernels for Structured Data, 2003, Lecture Notes in AI, vol. 2583, pp. 66-83.
Srinivasan et al., Feature Construction With Inductive Logic Programming: A Study of Quantitative Predictions of Biological Activity Aided by Structural Attributes, 1999, Data Mining and Knowledge Discovery, vol. 3, No. 1, pp. 37-57.
Muggleton et al., Support Vector Inductive Logic Programming, Oct. 2005, Lecture Notes is AI, vol. 3735, pp. 163-175.
Muggleton, Machine Learning for Systems Biology, Aug. 2005, Proceedings of the 15th Conference on Inductive Logic Programming, pp. 416-442.
Kramer et al., Bottom-Up Propositionalization, 2000, Proceedings of the ILP-2000 Work-In-Progress Track, pp. 156-162. Demiriz et al., Support Vector Machine Regression in Chemometrics, Jun. 2001, Proceedings of the 33rd Symposium on the Interface of Computing Science and Statistics, vol. 33, pp. 1-9.
Gartner et al., Multi-Instance Kernels, 2002, Proceedings of the 19th International Conference on Machine Learning, p. 176-186.
International Search Report for PCT/GB2006/003320.

*Primary Examiner* — Jeffrey A Gaffin
*Assistant Examiner* — Luis Sitiriche
(74) *Attorney, Agent, or Firm* — Brooks Kushman P.C.

(57) ABSTRACT

A computer implemented method of particular, although not exclusive application to analysing a plurality of molecules which comprises computing a kernel function for each pair of the plurality of molecules, the kernel function being representative of the number of features present in both molecules of the pairs and using the kernel function in a kernel based learning algorithm to model the relationship between the features and a property of the molecules. The method is also applicable to predicting a numerical value representing a characteristic of a molecule and, more generally, modelling instances of data in a database. A particular, although again not exclusive application, is the prediction of toxicity of a molecule.

12 Claims, 1 Drawing Sheet m1: R = $NH_2$
m2: R = OH
m3: R = $OCH_3$
m4: R = $CH_3$
m5: R = $SO_3CH_3$
m6: R = $NO_2$
m7: R = CN m

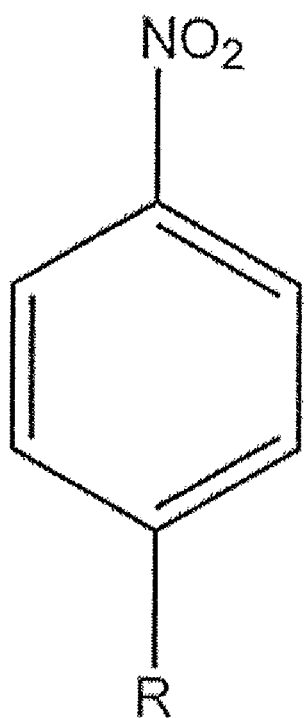
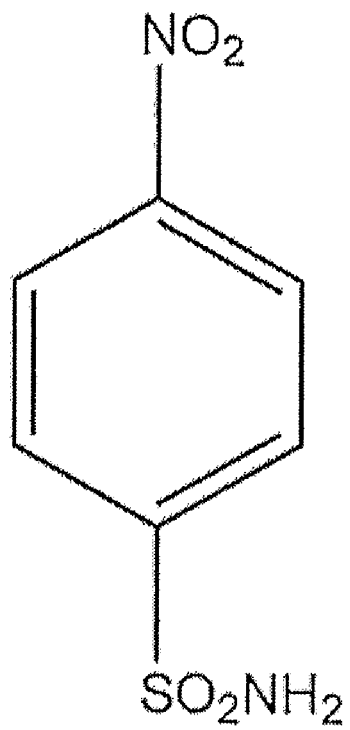
m1: R = NH$_2$
m2: R = OH
m3: R = OCH$_3$
m4: R = CH$_3$
m5: R = SO$_3$CH$_3$
m6: R = NO$_2$
m7: R = CN
m

SUPPORT VECTOR INDUCTIVE LOGIC PROGRAMMING

This invention relates to a learning method for analysing data and in particular to Support Vector Inductive Logic Programming (SVILP). SVILP is at the intersection of two areas of machine learning: namely Support Vector Machines (kernel-based methods) and inductive logic programming.

Inductive Logic Programming (ILP) is the area of Artificial Intelligence (AI) which deals with the induction of hypothesised predicate definitions. In ILP logic programs are used as a single representation for examples, background knowledge and hypotheses. ILP is differentiated from most other forms of Machine Learning (ML) both by its use of an expressive representation language and its ability to make use of logically encoded background knowledge. This has allowed successful applications of ILP in areas such as molecular biology (Turcotte, Muggleton, & Sternberg 2001; Cootes, Muggleton, & Sternberg 2003; King et al. 2004) and chemoinformatics (Finn et al. 1998; Sternberg & Muggleton 2003).

A logic program is a set of Horn clauses. Each Horn clause has the form Head<-Body. Thus the definite clause
active (X)<-charged (X), polar (X)
states that any X which is charged and polar is active. In this case, active, charged and polar are called "predicates", and are properties which are either true or false of X. This has allowed successful applications of ILP in areas such as molecular biology and natural language which both have rich sources of background knowledge and both benefit from the use of an expressive concept representation language.

Within ILP there has recently been interest in the development of kernels (as explained in the next paragraph) which incorporate relational information, for use within Support Vector Machines (SVMs). This addresses an inherent shortcoming of ILP in that it does not provide for an efficient representation of real valued outcomes, such as the toxicity of a drug. Rather, the strength of ILP lies in a Boolean logic that can represent complex relational structures. Combining the two approaches of ILP and SVMs results in a ML (machine learning) and more specificly AI (artificial intelligence) technique, SVILP that exploits relational structures to derive continuous, real-valued predictions.

Kernel based methods such as SVMs are attractive as their computational efficiency does not depend on the dimensionality of the feature space which is used. While, implicitly, SVMs rely on the calculation of a measure of similarity such as a dot product in the feature space, the calculation of the dot product is carried out using a kernel function which operates in the data space. Thus, for example, using SVMs with the well known radial basis function kernel allows an algorithm to learn a linear function in a feature space having an infinite number of dimensions. Since SVMs are well known in the art, both for classifications and regression (see for example "The nature of statistical learning theory", Vapnik, V, 1995, New York: Springer Verlag"), the theory and implementation of support vector regression/classification (SVR/C) will not be discussed in detail.

While SVM is a well-known analytical technique, it is crucial that the kernel used in an SVM is well adapted to the questions that are being addressed.

There is an existing approach (Gärtner, T., P. A. Flach, A. Kowalczyk, and A. J. Smola: 2002a, "Multi-Instance Kernels". In: *Proceedings of the Nineteenth International Conference on Machine Learning*, pp. 176-186, Morgan-Kaufmann; Gärtner, T., J. W. Lloyd, and P. A. Flach: 2002b, "Kernels for Structured Data". In: S. Matwin and C. Sammut (eds.): *Proceedings of the Twelfth International Conference on Inductive Logic Programming*. Berlin, pp. 66-83, Springer-Verlag) that incorporates relational information for use within SVMs. However the existing approach suffers from the drawback of being unable to make use of background knowledge. For example, in order to predict the toxicity of a molecule it relies on a very basic first order representation in which the features consist of the number of different types of atoms present in the molecule, the number of single bonds and the number of double and aromatic bonds. Thus, these features simply consist of the frequency of occurrence of atoms, bonds and atom pairs within the given molecule, which are used to form a vector representation of the molecule. More complicated representations which capture significantly more of the structural information derivable from a molecule have been thought to be computationally intractable.

There is thus at present no working method that allows complex ILP representations of the type described below to be combined with SVMs for complex tasks such as inference of real valued properties of data.

The invention is set out in the independent claims and further, optional, features of the invention are set out in the claims depending thereon.

Embodiments of the invention are now described, by way of example, and with reference to the accompanying figures in which:

FIG. 1 shows the structural formulae of 8 small molecules which are used to illustrate embodiments of the invention.

In an embodiment of the invention, an inference engine uses a combination of the (SVILP) kernel according to the invention with SVR (Support Vector Regression) to infer quantitative properties of new instances based on a database of instances with known quantitative properties and a set of clauses or features. In the specific example provided below the technique is applied to assessing the toxicity of a molecule.

FIG. 1 shows 8 exemplary molecules which will be used to describe the method according to embodiments of the invention. Seven molecules of known toxicity (m1, m2, . . . m7) are used to set up a database of non-instances, which is then used to predict the activity, or more specifically the toxicity of the molecule m. The clauses comprise a set of features which are believed to be relevant for the toxicity of a molecule, and in the specific embodiment are derived using an ILP system. In the example used to illustrate the method, the following six features (clauses) are used: an electron donating group (c1), a PI_bond connected to an oxygen atom (c2), a sulphur-oxygen double bond (c3), a bond between an aromatic atom and an SP3 carbon (c4), a bond between an aromatic atom and an SP3 oxygen atom (c5) and a $NO_2$ group and PI-bond connected to an oxygen atom (c6). Based on the representation of the molecule the clauses or features are implemented as logic programs in a manner known to the person skilled in the art and are held in a computer memory ready for further analysis.

In order to apply SVR in conjunction with ILP according to the invention, it is necessary to apply a kernel. The SVILP kernel described here is based on the idea that the more similar two instances are, the more hypothesised clauses can be expected to cover both (that is the clauses returning TRUE for both instances). An SVILP kernel providing a measure of similarity between two instances of data is thus implemented by considering the number of the clauses that apply to both instances.

The SVILP kernel can be implemented by populating a matrix X of size M×N, where M is the number of instances and N is the total number of clauses in a set (H), with the Boolean presence of each clause (h∈H) covering an instance.

Each of the M rows of X indicates which of the N clauses covers a given instance and is populated by entering a 1 in each column entry corresponding to an instance covered by the clause and a 0 in each column entry corresponding to an instance that is not covered by the clause.

In the example of FIG. 1, the following matrix X is obtained for the molecules (seven molecules (m1-m7) with known toxicity and one novel molecule (m)) and six clauses (c1-c6):

|    | c1 | c2 | c3 | c4 | c5 | C6 |
|----|----|----|----|----|----|----|
| M1 | 1  | 0  | 0  | 0  | 0  | 0  |
| M2 | 1  | 0  | 0  | 0  | 0  | 0  |
| M3 | 1  | 0  | 0  | 0  | 0  | 0  |
| M4 | 1  | 0  | 0  | 1  | 1  | 0  |
| M5 | 0  | 1  | 1  | 0  | 0  | 1  |
| M6 | 0  | 1  | 0  | 0  | 0  | 1  |
| M7 | 0  | 1  | 0  | 0  | 0  | 1  |
| M  | 0  | 1  | 1  | 0  | 0  | 1  |

A prior probability distribution is defined over the clauses. It allows the clauses to be weighted. $\tau$ is the function that gives the hypothesised clauses covering any particular instance and a function $f$ maps the set of hypothesised clauses to the probabilities.

The SVILP kernel is formed by $$K(m_i, m_j) = f(\tau(m_i) \cap \tau(m_j))$$

It can be shown that the kernel is an inner product in ILP space spanned by the hypothesised clauses which implies a mapping. Thus $f_k(m) = \sqrt{\pi(h_k(m))}$ for $k=1, \ldots, N$. The function $h_k(m)$ is a mapping from instances to labels {true, false} indicating if the clause k applies to instance m and $\pi$ are prior probabilities. The kernel can also be written in terms of inner products between mapped instances and is given by $$K(m_i, m_j) = \sum_{k=1}^{N} f_k(m_i) f_k(m_j)$$

Simplifying the expression $$K(m_i, m_j) = \sum_{k=1}^{N} \sqrt{\pi(x(i,k))} \cdot \sqrt{\pi(x(j,k))}$$

$$\left[ = \sum_{k=1}^{N} \pi x(i,k) x(j,k) \text{ given that } x(\cdot) = \{0, 1\} \right]$$

In a specific implementation a Radial Basis Function (RBF) version of the SVILP kernel is used:

$$K_{RBF} = \exp\left(-\frac{K(m_i, m_i) - 2K(m_i, m_j) + K(m_j m_j)}{2\sigma^2}\right),$$

where $\sigma$ is the spread of the RBF. This provides a measure of similarity being equal to one for identical instances and smaller otherwise. The number of theories applying both instances tends to increase the measure while the (total) number of theories applying to one or the other instance tends to decrease the measure.

Applying the kernel to the example of FIG. 1 and Table 1, the following kernel matrix for the value of K is obtained for uniform weights $\pi = \frac{1}{6} \approx 0.1667$:

|     | m1     | M2     | M3     | m4     | m5     | M6     | m7     |
|-----|--------|--------|--------|--------|--------|--------|--------|
| m1  | 1.0000 | 1.0000 | 1.0000 | 0.6411 | 0.4110 | 0.5133 | 0.5133 |
| m2  | 1.0000 | 1.0000 | 1.0000 | 0.6411 | 0.4110 | 0.5133 | 0.5133 |
| m3  | 1.0000 | 1.0000 | 1.0000 | 0.6411 | 0.4110 | 0.5133 | 0.5133 |
| m4  | 0.6411 | 0.6411 | 0.6411 | 1.0000 | 0.2635 | 0.3290 | 0.3290 |
| m5  | 0.4110 | 0.4110 | 0.4110 | 0.2635 | 1.0000 | 0.8007 | 0.8007 |
| m6  | 0.5133 | 0.5133 | 0.5133 | 0.3290 | 0.8007 | 1.0000 | 1.0000 |
| m7  | 0.5133 | 0.5133 | 0.5133 | 0.3290 | 0.8007 | 1.0000 | 1.0000 |

Given that K is a symmetric matrix, it is sufficient to calculate only the entries in the upper or lower triangle (i.e. $i=1, 2, \ldots, M$ and $j=i+1, i+2, \ldots, M$).

While the use of the kernel matrix in SVR is well known to the person skilled in the art, this will now be briefly described with reference to the example set out above. In order to apply the support vector technique to regression tasks a reasonable loss function is used. An $\epsilon$-insensitive loss function is a popular choice that is defined by $|t-F(m)|_\epsilon = \max(0, |t-F(m)|-\epsilon)$, where t is the actual toxicity and F(m) is the toxicity predicted by SVR. The loss function allows error below some $\epsilon > 0$ and controls the width of the insensitive band. Regression estimation is performed solving this optimisation problem. In essence, using SVR with this cost function consists in finding the "support vectors" (described below). The predicted toxicity of a new molecule is then found by a linear combination of the toxicities of the support vectors weighted by the respective distances, from the molecule, as measured by the kernel.

The regression function f, here the toxicity, is given by $$F(m) = \sum_{i=1}^{n} (a_i^* - a_i) K(m_i, m) + b$$

where $a_i$, and $a_i^*$ are Lagrange multipliers and b is the offset term.

Using a MATLAB™ implementation of SVR with the above-described RBF kernel and setting the parameters C, $\epsilon$ and $\sigma$ to 1.0, 0.2 and 0.25 respectively, the optimisation of the cost function in the present example yields four non-zero Lagrange multipliers $a_1^* = 1.000$, $\alpha_2^* = 0.1704$, $\alpha_5 = 0.1704$ and $\alpha_6 = 1.0000$. The corresponding instances or molecules m1, m2, m5 and m6 are known as support vectors. The offset term of the support vector regression equation above is b=3.3891.

Applying support vector regression to the new molecule m, the toxicity is found as F(m)=3.8792, which is close to the true toxicity t of the molecule of 3.908.

SVILP was evaluated empirically against related approaches, including an industry-standard toxin predictor called TOPKAT. Evaluation is conducted on a broad-ranging toxicity dataset DSSTox ("*Distributed Structure-Searchable Toxicity (DSSTox) Public Database Network: A Proposal*", Richard, A, and Williams, C, 2000, *Mutation Research* 499, 25-52). The dataset represents the most diverse set of toxins presently available in the public domain.

The DSSTox database contains organic and organometallic molecules with their toxicity values. The dataset consists of 576 molecules. Molecules in the form of SMILES strings, were transformed into 3D structures. All of the molecules contain continuous chemical feature known as the lowest unoccupied molecule orbital (LUMO), water/octanol partition coefficient (LOGP) and dipole moment. LOGP reflects the hydrophobicity of compounds and the mechanism of toxicities of these chemicals are based on their accumulation in the non-polar lipid phase of the biomembranes. LUMO and dipole moment can describe electrophilicities of compounds. The key information is given in the form of atom and bond description.

The performance of SVILP was compared using the RFB implementation of the SVILP kernel with a number of related techniques including partial least squares (PLS), multi instance kernels (MIK), an RBF kernel using only 3 chemical features (LOGP, LUMO, dipole moment), referred to as CHEM in the remainder. We also compared the performance of SVILP with well known Quantative-Structure Activity Relationship (QSAR) software TOPKAT (Toxicity Prediction by Komputer Assisted Technology).

The experimental methodology used 5-fold cross validation, splitting the data into five parts or folds. For evaluation we used mean squared error (MSE) and R-squared (a standard measure of accuracy in QSAR). C (regularization parameter), $\epsilon$ (controls width of insensitive band), and $\sigma$ (width of Gaussian) are the tunable parameters for kernel-based methods (SVILP, CHEM & MIK). In PLS the tunable parameter is "the number of components". These parameters can be set by some model selection method. The traditional protocol to set the values for the parameters is the minimisation (or maximisation) of some criterion relative to the values of both parameters using a validation set.

The optimal values of the tunable parameters were set using a validation set as described. The parameters for each fold is set using only the training set of the fold by randomly selecting a subset comprising 75% of the data (training set of each fold) for the training set and using the remaining data as a test set. Sets covering a range of values of the parameters were selected. The sets of the values are given by C={10, 100, 1000, 10000}, $\epsilon$={0.1, 0.3, 0.5, 1.0} and $\sigma$={0.125, 0.25, 0.5, 4, 16}.

For PLS the number of components ranged from 1 to 15. The parameters which give the minimum MSE on the validation set were chosen. For the selected parameters the models (created by the methods described above) were obtained using a full training set and their performance was evaluated on test compounds.

In order to perform the prediction task using SVILP, we first obtained a set of clauses. Examples and Background knowledge (atom-bond, high level chemical groups e.g. phenyl ring, aldehyde, carboxylic acids and chemical features) are given to CProgol5.0 [Muggleton, S. Inverse entailment and Progol. New Generation Computing 13 (1995) 245-286] which generates a set of clauses.

For all the folds, the clauses with positive compression (measure of information) were selected where the number of obtained clauses for each fold can vary between 1500-2000. The compression value of a clause is given by $$V = \frac{P*(p-(n+c+h))}{p},$$

where p is the number of positive instances correctly deducible from the clause, n is the number of negative examples incorrectly deducible from the clause, c is the length of the clause and h is number of further atoms to complete the input/output connectivity of the clause and P is the total number of positive examples.

The hypothesised clauses are then taken by a Prolog program which computes the hypothesis-instance association indicating for each instance the set of all hypothesised clauses which imply it. In this work a uniform prior probability distribution over the clauses was used. Then the similarity between molecules was computed using the SVILP kernel. In order to apply PLS for toxicity prediction, the same set of hypothesised clauses generated by CProgol5.0 as for SVILP was used.

The SVM package SVMTorch ("SVMTorch: Support vector machine for large-scale regression problems", Collobert, R, and Bengio, S, 2001, Journal of Machine Learning Research 1, 143-160) was used for the experiments.

A series of experiments was conducted to evaluate the performance of SVILP. A first set of experiments was conducted to evaluate the efficacy of the SVILP approach for predicting the toxicity values as compared to the other approaches. Table 1 shows the results. The results are averaged over 5 runs of the methods. Based on the statistical sign test method, SVILP shows significant improvement in comparison with the other methods.

TABLE 1

MSE and R-squared for CHEM, PLS, MIK and SVILP.

|  | MSE | R-squared |
|---|---|---|
| CHEM | 0.811 | 0.519 |
| PLS | 0.671 | 0.593 |
| MI | 0.838 | 0.503 |
| SVILP | 0.574 | 0.655 |

In a second set of experiments the performance of the methods for qualitative prediction was assessed. The SVILP approach was evaluated by employing it for categorising the molecules into two categories, toxic and non-toxic. The performance of SVILP was compared with the standard ILP system CProgol5.0. All of the methods predict the non-toxic molecules with high accuracy. Table 2 shows the results for the category "toxic". According to a McNemar test, the SVILP method shows significant improvement with respect to the other methods.

TABLE 2

Accuracy for ILP, CHEM, PLS, MI and SVILP for qualitative prediction (classification).

|  | Accuracy (%) |
|---|---|
| ILP (CPrOGOL5,0) | 55 |
| CHEM | 58 |
| PLS | 71 |
| MI | 60 |
| SVILP | 73 |

Finally SVILP was compared with TOPKAT. The software accepts the structures of the molecules in SMILES string and automatically split the molecule into different fragments, and then uses these fragments as well as some chemical descriptors such as LOGP and shape index for predictions. In order to make a fair comparison of the above methods with the commercial software TOPKAT, it must be ensured that only predicted accuracies for molecules that were not included in the training data of either method are considered. Accordingly, any of the DSSTox molecules that TOPKAT had in its database were excluded leaving 165 unseen molecules.

Table 3 shows the results. According to sign test, the SVILP shows significant improvement in comparison with all of the other approaches. Our results show that SVILP outperforms all the other methods in the study. The results confirm the efficacy and usefulness of our approach.

TABLE 3

MSE and R-squared for CHEM, PLS, TOPKAT and SVILP.

|        | MSE  | R-squared |
|--------|------|-----------|
| CHEM   | 1.04 | 0.48      |
| PLS    | 1.03 | 0.47      |
| TOPKAT | 2.2  | 0.26      |
| SVILP  | 0.8  | 0.57      |

It is understood that the kernels described above are not limited to the use in conjunction with SVMs, they can also be used in conjunction with other techniques such as Kernel CCA, Kernel PCA and Gaussian processors. Although the invention has been described in relation to embodiments for analysing the toxicity of molecules, it is understood that the invention is equally applicable to any other measure of activity of a molecule or indeed the prediction of a numeric property of any other class of object, for example biochemical networks. The invention can be implemented in any appropriate manner for example software, hardware or firmware and applied to any appropriate problem.

The invention claimed is:

1. A computer implemented method of modelling a numerical property of a molecule, the method comprising:
   a) automatically defining a plurality of clauses implemented as logic programs having a Boolean output, by automated hypothesising of inductive logic programming clauses based on the molecule;
   b) applying the logic programs to a plurality of molecules having a known value of the numerical property to derive a Boolean output of each logic program for each molecule to populate a matrix X of size M×N, where M is the number of molecules and N is the number of clauses;
   c) computing a kernel function which provides a measure of similarity between each pair of the plurality of molecules having a known value of the numerical property, the kernel function being a function of the number of logic programs of which the output is Boolean TRUE for both molecules of the pairs, wherein the value of the kernel function increases with the number of Boolean outputs which are TRUE for both molecules of the pair of molecules and decreases with the number of Boolean outputs which are TRUE for one or other of the pair of molecules; and
   d) using the kernel function to derive a support vector regression model of the relationship between the clauses and the numerical property of the molecules using support vector regression.

2. A method as claimed in claim 1, wherein the numerical property is toxicity.

3. A computer-implemented method of predicting a numerical value representing a characteristic of a molecule having a plurality of features, the method comprising:
   a) automatically defining a plurality of features in the form of clauses implemented as logic programs having a Boolean output, by automated hypothesising of inductive logic programming clauses based on the molecule;
   b) applying the logic programs to a plurality of molecules having a known numerical value and said molecule to derive a Boolean output of each logic program for each molecule to populate a matrix X of size M×N, where M is the number of molecules and N is the number of clauses
   c) calculating, using support a predicted value for said molecule using the output of a kernel function for the said molecule and a known molecule having a plurality of features, wherein the kernel function provides a measure of similarity between each pair of the plurality of molecules, wherein the kernel function is representative of the numbers of Boolean outputs which are TRUE in both molecules and wherein the value of the kernel function increases with the number of Boolean outputs which are TRUE for both molecules of the pair of molecules and decreases with the number of Boolean outputs which are TRUE for one or other of the pair of molecules.

4. A method as claimed in claim 3, wherein the predicted value for said molecule is derived from a linear combination of the numerical values of the corresponding molecules having known values weighted by the respective distances from the molecule as defined by the kernel function.

5. A computer-implemented method of analysing a numerical property molecule, the method comprising:
   a) automatically defining a plurality of clauses implemented as logic programs having a Boolean output, by automated hypothesising of inductive logic programming clauses based on the molecule;
   b) applying the logic programs to a plurality of molecules having a known value of the numerical property to derive a Boolean output of each logic program for each molecule;
   c) computing a kernel function which provides a measure of similarity between each pair of the plurality of molecules, the kernel function being representative of the number of Boolean outputs which are TRUE for in both instances molecules of the pair and wherein a prior probability distribution is defined over the clauses whereby the clauses are weighted and wherein the kernel function is formed from an Support Vector Inductive Logic Programming (SVILP) kernel $K(m_i, m_j)$ $$K(m_i, m_j) = f(\tau(m_i) \cap \tau(m_j))$$

where $\tau$ is the function that gives the clauses covering any particular molecule and $f$ is the function which maps the set of clauses to the probabilities; and
   d) using the kernel function in a support vector regression algorithm to model the relationship between the clauses and the numerical property of the molecules.

6. A method as claimed in claim 1, wherein a prior probability distribution is defined over the clauses whereby clauses are weighted.

7. A computer system adapted to implement a method as claimed in claim 1.

8. A non-transitory computer readable storage medium having instructions stored thereon to implement the computer implemented method of claim 1.

9. A method as claimed in claim 6, wherein the kernel function is formed from an Support Vector Inductive Logic Programming (SVILP) kernel $K(m_i, m_j)$ $$K(m_i, m_j) = f(\tau(m_i) \cap \tau(m_j))$$

where $\tau$ is the function that gives the clauses covering any particular molecule and $f$ is the function which maps the set of clauses to the probabilities.

10. A method as claimed in claim 9, wherein the kernel function is implemented as a Radial Basis Function (RBF) version of the SVILP kernel:

$$K_{RBF} = \exp\left(-\frac{K(m_i, m_i) - 2K(m_i, m_j) + K(m_j, m_j)}{2\sigma^2}\right).$$

11. A method as claimed in claim 10, wherein the Radial Basis Function (RBF) version of the kernel is expressed as a symmetric matrix of size M×M where M is the number of molecules and each entry in the matrix is a measure of similarity between each pair of molecules with the measure of similarity being equal to one for identical instances and smaller otherwise.

12. A method as claimed in claim 5, wherein applying the logic programs to the plurality of molecules having a known value of the numerical property to derive a Boolean output of each logic program for each molecule comprising populating a matrix X of size M×N, where M is the number of molecules and N is the number of clauses.

* * * * *

UNITED STATES PATENT AND TRADEMARK OFFICE
CERTIFICATE OF CORRECTION

PATENT NO. : 8,126,823 B2
APPLICATION NO. : 12/066689
DATED : February 28, 2012
INVENTOR(S) : Muggleton et al.

Page 1 of 1

It is certified that error appears in the above-identified patent and that said Letters Patent is hereby corrected as shown below:

Column 8, Line 23, Claim 5:

After "analysing a numerical property" insert -- of a --.

Column 8, Line 36, Claim 5:

Delete "which are TRUE for in both instances"

And insert therefor -- which are TRUE for both --.

Signed and Sealed this
Eighth Day of May, 2012

David J. Kappos
*Director of the United States Patent and Trademark Office*